United States Patent
Liu et al.

(10) Patent No.: US 11,976,267 B2
(45) Date of Patent: May 7, 2024

(54) **RECOMBINANT *ESCHERICHIA COLI* STRAIN FOR PRODUCING SUCCINIC ACID AND CONSTRUCTION METHOD THEREOF**

(71) Applicant: JIANGNAN UNIVERSITY, Wuxi (CN)

(72) Inventors: Liming Liu, Wuxi (CN); Wenxiu Tang, Wuxi (CN); Chen Shen, Wuxi (CN); Qiuling Luo, Wuxi (CN); Xiulai Chen, Wuxi (CN); Jia Liu, Wuxi (CN); Cong Gao, Wuxi (CN); Wei Song, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 694 days.

(21) Appl. No.: 17/256,906

(22) PCT Filed: Nov. 12, 2020

(86) PCT No.: PCT/CN2020/128254
§ 371 (c)(1),
(2) Date: Dec. 29, 2020

(87) PCT Pub. No.: WO2022/088263
PCT Pub. Date: May 5, 2022

(65) Prior Publication Data
US 2022/0235314 A1    Jul. 28, 2022

(51) Int. Cl.
| | |
|---|---|
| C12N 1/20 | (2006.01) |
| C12N 9/02 | (2006.01) |
| C12N 9/10 | (2006.01) |
| C12N 9/88 | (2006.01) |
| C12N 15/52 | (2006.01) |
| C12P 1/04 | (2006.01) |
| C12R 1/19 | (2006.01) |

(52) U.S. Cl.
CPC ........... *C12N 1/205* (2021.05); *C12N 9/0004* (2013.01); *C12N 9/1025* (2013.01); *C12N 9/88* (2013.01); *C12N 15/52* (2013.01); *C12P 1/04* (2013.01); *C12R 2001/19* (2021.05)

(58) Field of Classification Search
None
See application file for complete search history.

(56) References Cited

U.S. PATENT DOCUMENTS

2008/0293101 A1* 11/2008 Peters ................. C12N 9/0036
435/157

FOREIGN PATENT DOCUMENTS

| | | | |
|---|---|---|---|
| CN | 102282156 A | 12/2011 | |
| CN | 104694449 A | 6/2015 | |
| CN | 104974946 A | 10/2015 | |
| CN | 105658801 A | 6/2016 | |
| CN | 105779513 A | 7/2016 | |
| WO | WO-03072726 A2 * | 9/2003 | ........... C12N 9/0004 |

OTHER PUBLICATIONS

Olajuyin et al. (Bioresource Technology, 214, pp. 653-659, 2016).*
Yong Yu et al., "Construction of an energy-conserving glycerol utilization pathways for improving anaerobic succinate production in *Escherichia coli*" Metabolic Engineering 56 (2019) 181-189 (Oct. 7, 2019).
Fangfang, Yue et al., "Construction of engineered *Escherichia coli* for succinate producition" China Brewing, No. 2, pp. 25-29 (Feb. 15, 2010).

* cited by examiner

*Primary Examiner* — Richard G Hutson
(74) *Attorney, Agent, or Firm* — SZDC Law PC (57) ABSTRACT

The invention provides a recombinant *Escherichia coli* strain for producing succinic acid and a construction method thereof. The by-product encoding genes in the *E. coli* strain FMME-N-2 are knocked out to obtain the *E. coli* strain FMME-N-5 (ΔfocA-pflB-ΔldhA-Δpta-ackA); and the phosphoenolpyruvate carboxykinase pck derived from *Actinobacillus succinogenes* and the phosphite dehydrogenase ptxD derived from *Pseudomonas stutzeri* were overexpressed. The constructed plasmid pTrcHisA-pck-ptxD was introduced into the expression host *E. coli* FMME-N-5 (ΔfocA-pflB-ΔldhA-Δpta-ackA), and the cells were screened in a plate containing ampicillin, to obtain an engineered strain *E. coli* FMME-N-5 (ΔfocA-pflB-ΔldhA-Δpta-ackA)-pck-ptxD that can efficiently produce succinic acid. After fermentation by a two-stage fermentation strategy, the production of succinic acid reaches 137 g/L, the yield of succinic acid is up to 1 g/g glucose, and the space time yield is 1.43 g/L/h, while no by-products of lactic acid and formic acid are accumulated, and the acetic acid content is 1-2 g/L.

10 Claims, 3 Drawing Sheets
Specification includes a Sequence Listing.

SEQUENCE LISTING

<160> NUMBER OF SEQ ID NOS: 17

<210> SEQ ID NO 1
<211> LENGTH: 1617
<212> TYPE: DNA
<213> ORGANISM: Artificial Sequence
<220> FEATURE:
<223> OTHER INFORMATION: Phosphoenolpyruvate carboxykinase

<400> SEQUENCE: 1

```
atgactgact taaacaaact cgttaaagaa cttaatgact tagggcttac cgatgttaag      60
gaaattgtgt ataacccgag ttatgaacaa cttttcgagg aagaaaccaa accgggtttg     120
gagggtttcg ataaagggac gttaaccacg cttggcgcgg ttgccgtcga tacggggatt     180
tttaccggtc gttcaccgaa agataaatat atcgtttgcg atgaaactac gaaagacacc     240
gtttggtgga acagcgaagc ggcgaaaaac gataacaaac cgatgacgca agaaacttgg     300
aaaagtttga gagaattagt ggcgaaacaa ctttccggta aacgtttatt cgtggtagaa     360
ggttactgcg gcgccagtga aaacaccgt atcggtgtgc gtatggttac tgaagtggca     420
tggcaggcgc attttgtgaa aaacatgttt atccgaccga ccgatgaaga gttgaaaaat     480
ttcaaagcgg attttaccgt gttaaacggt gctaaatgta ctaatccgaa ctggaaagaa     540
caaggtttga acagtgaaaa ctttgtcgct ttcaatatta ccgaaggtat tcagcttatc     600
ggcggtactt ggtacggcgg tgaaatgaaa aaaggtatgt tctcaatgat gaactacttc     660
ctgccgttaa aaggtgtggc ttccatgcac tgttccgcca acgtaggtaa agacggtgac     720
gtggctattt tcttcggttt atccggtacg ggtaaaacaa cgctttcgac cgatcctaaa     780
cgccaattaa tcggtgatga cgaacacggt tgggatgaat ccggcgtatt taactttgaa     840
ggcggttgtt acgcgaaaac cattaactta tctcaagaaa cgaaccgga tatttacggc     900 gcaatccgtc gtgacgcatt attagaaaac gtcgtggttc gtgcagacgg ttccgttgac     960
tttgacgacg gttcaaaaac agaaaatacc cgtgtttcat atccgattta ccacatcgac    1020
aacatcgttc gtccggtatc gaaagccggt catgcaacca agtgattttt cttaaccgcg    1080
gacgcattcg gcgtattgcc gccggtttca aaactgactc cggaacaaac cgaatactac    1140
ttcttatccg gctttactgc aaaattagcg ggtacggaac gcggcgtaac cgaaccgact    1200
ccgacattct cggcctgttt cggtgcggca ttcttaagcc tgcatccgat tcaatatgcg    1260
```

| | |
|---|---|
| gacgtgttgg tcgaacgcat gaaagcctcc ggtgcggaag cttatttggt gaacaccggt | 1320 |
| tggaacggca cgggtaaacg tatttcaatc aaagataccc gcggtattat cgatgcgatt | 1380 |
| ttggacggtt caatcgaaaa agcggaaatg ggcgaattgc caatctttaa tttagcgatt | 1440 |
| cctaaagcat taccgggtgt tgatcctgct attttggatc cgcgcgatac ttacgcagac | 1500 |
| aaagcgcaat ggcaagttaa agcggaagat ttggcaaacc gtttcgtgaa aactttgtg | 1560 |
| aaatatacgg cgaatccgga agcggctaaa ttagttggcg ccggtccaaa agcataa | 1617 |

<210> SEQ ID NO 2
<211> LENGTH: 1011
<212> TYPE: DNA
<213> ORGANISM: Artificial Sequence
<220> FEATURE:
<223> OTHER INFORMATION: Phosphite dehydrogenase

<400> SEQUENCE: 2

| | |
|---|---|
| atgctgccga aactggtgat cacgcatcgc gtgcacgacg aaattctcca gctcctcgcg | 60 |
| ccacattgcg aactgatgac gaaccagacc gatagcacgc tgacccgcga agaaattctg | 120 |
| cgtcgctgcc gtgatgcgca agcgatgatg gcctttatgc cggatcgcgt tgatgccgac | 180 |
| tttctgcaag cgtgcccaga actgcgtgtt gttggctgcg ccctcaaagg cttcgacaac | 240 |
| ttcgacgtgg atgcgtgcac ggcccgtggc gtttggctga cctttgtgcc ggatctgctg | 300 |
| accgttccga ccgcggaact ggcgattggt ctggccgtgg gtctcggtcg tcatctgcgt | 360 |
| gcggccgacg ccttcgttcg tagcggcgag ttccaaggct ggcagccgca gttctacggc | 420 |
| accggtctgg ataatgccac cgttggtatc ctcggcatgg gtgcgatcgg tctggcgatg | 480 |
| gcggatcgtc tgcaaggctg gggtgccacc ctccagtatc atgaagcgaa ggcgctggat | 540 |
| acgcaaaccg aacagcgcct cggtctgcgt caagttgcgt gcagcgagct gttcgccagt | 600 |
| agcgatttca ttctgctcgc gctgccgctc aacgcggata cccagcatct cgttaacgcc | 660 |
| gaactgctgg cgctggttcg tccgggcgcg ctgctggtga cccgtgccg tggtagtgtg | 720 |
| gttgatgaag ccgccgttct cgccgcgctg aacgtggtc aactgggcgg ttacgccgcc | 780 |
| gacgtttttg agatggaaga ttgggcgcgt gcggaccgtc cacgtctgat cgatccggcg | 840 |
| ctgctggccc atccaaacac gctgttcacg ccgcatatcg tagtgccgt tcgtgccgtg | 900 |
| cgtctggaaa tcgaacgctg cgcggcgcag aatatcatcc aagttctcgc cggtgcccgc | 960 |
| ccaattaatg ccgccaatcg tctgccaaaa gccgaaccag cggcgtgcta a | 1011 |

<210> SEQ ID NO 3
<211> LENGTH: 2283
<212> TYPE: DNA
<213> ORGANISM: Artificial Sequence
<220> FEATURE:
<223> OTHER INFORMATION: Pyruvate formate lyase

<400> SEQUENCE: 3

| | |
|---|---|
| atgtccgagc ttaatgaaaa gttagccaca gcctgggaag ttttaccaa aggtgactgg | 60 |
| cagaatgaag taaacgtccg tgacttcatt cagaaaaact acactccgta cgagggtgac | 120 |
| gagtccttcc tggctggcgc tactgaagcg accaccaccc tgtgggacaa agtaatggaa | 180 |
| ggcgttaaac tggaaaaccg cactcacgcg ccagttgact ttgacaccgc tgttgcttcc | 240 |
| accatcacct ctcacgacgc tggctacatc aacaagcagc ttgagaaaat cgttggtctg | 300 |
| cagactgaag ctccgctgaa acgtgctctt atcccgttcg gtggtatcaa aatgatcgaa | 360 |

| ggttcctgca | aagcgtacaa | ccgcgaactg | gatccgatga | tcaaaaaaat | cttcactgaa | 420 |
| taccgtaaaa | ctcacaacca | gggcgtgttc | gacgtttaca | ctccggacat | cctgcgttgc | 480 |
| cgtaaatctg | gtgttctgac | cggtctgcca | gatgcatatg | gccgtggccg | tatcatcggt | 540 |
| gactaccgtc | gcgttgcgct | gtacggtatc | gactacctga | tgaaagacaa | actggcacag | 600 |
| ttcacttctc | tgcaggctga | tctggaaaac | ggcgtaaacc | tggaacagac | tatccgtctg | 660 |
| cgcgaagaaa | tcgctgaaca | gcaccgcgct | ctgggtcaga | tgaaagaaat | ggctgcgaaa | 720 |
| tacggctacg | acatctctgg | tccggctacc | aacgctcagg | aagctatcca | gtggacttac | 780 |
| ttcggctacc | tggctgctgt | taagtctcag | aacggtgctg | caatgtcctt | cggtcgtacc | 840 |
| tccaccttcc | tggatgtgta | catcgaacgt | gacctgaaag | ctggcaagat | caccgaacaa | 900 |
| gaagcgcagg | aaatggttga | ccacctggtc | atgaaactgc | gtatggttcg | cttcctgcgt | 960 |
| actccggaat | acgatgaact | gttctctggc | gacccgatct | gggcaaccga | atctatcggt | 1020 |
| ggtatgggcc | tcgacggtcg | taccctggtt | accaaaaaca | gcttccgttt | cctgaacacc | 1080 |
| ctgtacacca | tgggtccgtc | tccggaaccg | aacatgacca | ttctgtggtc | tgaaaaactg | 1140 |
| ccgctgaact | tcaagaaatt | cgccgctaaa | gtgtccatcg | acacctcttc | tctgcagtat | 1200 |
| gagaacgatg | acctgatgcg | tccggacttc | aacaacgatg | actacgctat | tgcttgctgc | 1260 |
| gtaagcccga | tgatcgttgg | taaacaaatg | cagttcttcg | gtgcgcgtgc | aaacctggcg | 1320 |
| aaaaccatgc | tgtacgcaat | caacggcggc | gttgacgaaa | aactgaaaat | gcaggttggt | 1380 |
| ccgaagtctg | aaccgatcaa | aggcgatgtc | ctgaactatg | atgaagtgat | ggagcgcatg | 1440 |
| gatcacttca | tggactggct | ggctaaacag | tacatcactg | cactgaacat | catccactac | 1500 |
| atgcacgaca | gtacagctac | gaagcctctc | tgatggcgc | tgcacgaccg | tgacgttatc | 1560 |
| cgcaccatgg | cgtgtggtat | cgctggtctg | tccgttgctg | ctgactccct | gtctgcaatc | 1620 |
| aaatatgcga | agttaaaacc | gattcgtgac | gaagacggtc | tggctatcga | cttcgaaatc | 1680 |
| gaaggcgaat | acccgcagtt | tggtaacaat | gatccgcgtg | tagatgacct | ggctgttgac | 1740 |
| ctggtagaac | gtttcatgaa | gaaaattcag | aaactgcaca | cctaccgtga | cgctatcccg | 1800 |
| actcagtctg | ttctgaccat | cacttctaac | gttgtgtatg | gtaagaaaac | gggtaacacc | 1860 |
| ccagacggtc | gtcgtgctgg | cgcgccgttc | ggaccgggtg | ctaacccgat | gcacggtcgt | 1920 |
| gaccagaaag | gtgcagtagc | ctctctgact | tccgttgcta | aactgccgtt | tgcttacgct | 1980 |
| aaagatggta | tctcctacac | cttctctatc | gttccgaacg | cactgggtaa | agacgacgaa | 2040 |
| gttcgtaaga | ccaacctggc | tggtctgatg | gatggttact | tccaccacga | agcatccatc | 2100 |
| gaaggtggtc | agcacctgaa | cgttaacgtg | atgaaccgtg | aaatgctgct | cgacgcgatg | 2160 |
| gaaaacccgg | aaaaatatcc | gcagctgacc | atccgtgtat | ctggctacgc | agtacgtttc | 2220 |
| aactcgctga | ctaaagaaca | gcagcaggac | gttattactc | gtaccttcac | tcaatctatg | 2280 |
| taa | | | | | | 2283 |

<210> SEQ ID NO 4
<211> LENGTH: 990
<212> TYPE: DNA
<213> ORGANISM: Artificial Sequence
<220> FEATURE:
<223> OTHER INFORMATION: Lactate dehydrogenase

<400> SEQUENCE: 4

| atgaaactcg | ccgtttatag | cacaaaacag | tacgacaaga | agtacctgca | acaggtgaac | 60 |
| gagtcctttg | gctttgagct | ggaattttt | gactttctgc | tgacggaaaa | aaccgctaaa | 120 |

```
actgccaatg gctgcgaagc ggtatgtatt ttcgtaaacg atgacggcag ccgcccggtg      180
ctggaagagc tgaaaaagca cggcgttaaa tatatcgccc tgcgctgtgc cggtttcaat      240
aacgtcgacc ttgacgcggc aaaagaactg gggctgaaag tagtccgtgt tccagcctat      300
gatccagagg ccgttgctga acacgccatc ggtatgatga tgacgctgaa ccgccgtatt      360
caccgcgcgt atcagcgtac ccgtgatgct aacttctctc tggaaggtct gaccggcttt      420
actatgtatg gcaaaacggc aggcgttatc ggtaccggta aaatcggtgt ggcgatgctg      480
cgcattctga aaggttttgg tatgcgtctg ctggcgttcg atccgtatcc aagtgcagcg      540
gcgctggaac tcggtgtgga gtatgtcgat ctgccaaccc tgttctctga atcagacgtt      600
atctctctgc actgcccgct gacaccggaa actatcatc tgttgaacga agccgccttc       660
gaacagatga aaaatggcgt gatgatcgtc aataccagtc gcggtgcatt gattgattct      720
caggcagcaa ttgaagcgct gaaaaatcag aaaattggtt cgttgggtat ggacgtgtat      780
gagaacgaac gcgatctatt ctttgaagat aaatccaacg acgtgatcca ggatgacgta      840
ttccgtcgcc tgtctgcctg ccacaacgtg ctgtttaccg gcaccaggc attcctgaca       900 gcagaagctc tgaccagtat ttctcagact acgctgcaaa acttaagcaa tctggaaaaa      960
ggcgaaacct gcccgaacga actggtttaa                                      990
```

<210> SEQ ID NO 5
<211> LENGTH: 2145
<212> TYPE: DNA
<213> ORGANISM: Artificial Sequence
<220> FEATURE:
<223> OTHER INFORMATION: Phosphotransacetylase

<400> SEQUENCE: 5

```
gtgtcccgta ttattatgct gatccctacc ggaaccagcg tcggtctgac cagcgtcagc       60
cttggcgtga tccgtgcaat ggaacgcaaa ggcgttcgtc tgagcgtttt caaacctatc      120
gctcagccgc gtaccggtgg cgatgcgccc gatcagacta cgactatcgt gcgtgcgaac      180
tcttccacca cgacggccgc tgaaccgctg aaaatgagct acgttgaagg tctgctttcc      240
agcaatcaga aagatgtgct gatggaagag atcgtcgcaa actaccacgc taacaccaaa      300
gacgctgaag tcgttctggt tgaaggtctg gtcccgacac gtaagcacca gtttgcccag      360
tctctgaact acgaaatcgc taaaacgctg aatgcgaaa tcgtcttcgt tatgtctcag       420
ggcactgaca ccccggaaca gctgaaagag cgtatcgaac tgacccgcaa cagcttcggc      480
ggtgccaaaa acaccaacat caccggcgtt atcgttaaca aactgaacgc accggttgat      540
gaacagggtc gtactcgccc ggatctgtcc gagattttcg acgactcttc caaagctaaa      600
gtaaacaatg ttgatccggc gaagctgcaa gaatccagcc cgctgccggt tctcggcgct      660
gtgccgtgga gctttgacct gatcgcgact cgtgcgatcg atatggctcg ccacctgaat      720
gcgaccatca tcaacgaagg cgacatcaat actcgccgcg ttaaatccgt cactttctgc      780
gcacgcagca ttccgcacat gctggagcac ttccgtgccg ttctctgct ggtgacttcc      840 gcagaccgtc ctgacgtgct ggtggccgct gcctggcag ccatgaacgg cgtagaaatc       900
ggtgccctgc tgctgactgg cggttacgaa atggacgcgc gcatttctaa actgtgcgaa      960
cgtgctttcg ctaccggcct gccggtattt atggtgaaca ccaacacctg gcagacctct     1020
ctgagcctgc agagcttcaa cctggaagtt ccggttgacg atcacgaacg tatcgagaaa     1080
gttcaggaat acgttgctaa ctacatcaac gctgactgga tcgaatctct gactgccact     1140
```

```
tctgagcgca gccgtcgtct gtctccgcct gcgttccgtt atcagctgac tgaacttgcg    1200
cgcaaagcgg gcaaacgtat cgtactgccg gaaggtgacg aaccgcgtac cgttaaagca    1260
gccgctatct gtgctgaacg tggtatcgca acttgcgtac tgctgggtaa tccggcagag    1320
atcaaccgtg ttgcagcgtc tcagggtgta gaactgggtg cagggattga aatcgttgat    1380
ccagaagtgg ttcgcgaaag ctatgttggt cgtctggtcg aactgcgtaa gaacaaaggc    1440
atgaccgaaa ccgttgcccg cgaacagctg gaagacaacg tggtgctcgg tacgctgatg    1500
ctggaacagg atgaagttga tggtctggtt tccggtgctg ttcacactac cgcaaacacc    1560
atccgtccgc cgctgcagct gatcaaaact gcaccgggca gctccctggt atcttccgtg    1620
ttcttcatgc tgctgccgga acaggtttac gtttacggtg actgtgcgat caacccggat    1680
ccgaccgctg aacagctggc agaaatcgcg attcagtccg ctgattccgc tgcggccttc    1740
ggtatcgaac cgcgcgttgc tatgctctcc tactccaccg gtacttctgg tgcaggtagc    1800
gacgtagaaa aagttcgcga agcaactcgt ctggcgcagg aaaaacgtcc tgacctgatg    1860
atcgacggtc cgctgcagta cgacgctgcg gtaatggctg acgttgcgaa atccaaagcg    1920
ccgaactctc cggttgcagg tcgcgctacc gtgttcatct cccggatct gaacaccggt    1980 aacaccacct acaaagcggt acagcgttct gccgacctga tctccatcgg gccgatgctg    2040
cagggtatgc gcaagccggt taacgacctg tcccgtggcg cactggttga cgatatcgtc    2100
tacaccatcg cgctgactgc gattcagtct gcacagcagc agtaa                    2145

<210> SEQ ID NO 6
<211> LENGTH: 65
<212> TYPE: DNA
<213> ORGANISM: Artificial Sequence
<220> FEATURE:
<223> OTHER INFORMATION: Primer pflB-focA-S

<400> SEQUENCE: 6
ttactccgta tttgcataaa aaccatgcga gttacgggcc tataagtgta ggctggagct    60
gcttc                                                                65

<210> SEQ ID NO 7
<211> LENGTH: 65
<212> TYPE: DNA
<213> ORGANISM: Artificial Sequence
<220> FEATURE:
<223> OTHER INFORMATION: Primer pflB-focA-A

<400> SEQUENCE: 7
atagattgag tgaaggtacg agtaataacg tcctgctgct gttctcatat gaatatcctc    60
cttag                                                                65

<210> SEQ ID NO 8
<211> LENGTH: 65
<212> TYPE: DNA
<213> ORGANISM: Artificial Sequence
<220> FEATURE:
<223> OTHER INFORMATION: Primer ldhA-S

<400> SEQUENCE: 8
atgaactcgc cgttttatag cacaaaacag tacgacaaga agtacgtgta ggctggagct    60
gcttc                                                                65

<210> SEQ ID NO 9
<211> LENGTH: 65
```

```
<212> TYPE: DNA
<213> ORGANISM: Artificial Sequence
<220> FEATURE:
<223> OTHER INFORMATION: Primer ldhA-A

<400> SEQUENCE: 9
ttaaaccagt cgttcgggc aggtttcgcc tttttccaga ttgctcatat gaatatcctc    60
cttag                                                              65

<210> SEQ ID NO 10
<211> LENGTH: 66
<212> TYPE: DNA
<213> ORGANISM: Artificial Sequence
<220> FEATURE:
<223> OTHER INFORMATION: Primer pta-S

<400> SEQUENCE: 10
gtgtcccgta ttattatgct gatccctacc ggaaccagcg tcggtcgtgt aggctggagc    60
tgcttc                                                              66

<210> SEQ ID NO 11
<211> LENGTH: 68
<212> TYPE: DNA
<213> ORGANISM: Artificial Sequence
<220> FEATURE:
<223> OTHER INFORMATION: Primer pta-A

<400> SEQUENCE: 11
tacaccatcg cgctgactgc gattcagtct gcacagcagc agcagtaaca tatgaatatc    60
ctccttag                                                            68

<210> SEQ ID NO 12
<211> LENGTH: 65
<212> TYPE: DNA
<213> ORGANISM: Artificial Sequence
<220> FEATURE:
<223> OTHER INFORMATION: Primer pta-ackA-S

<400> SEQUENCE: 12
atgtcgagta agttagtact ggttctgaac tgcggtagtt cttcagtgta ggctggagct    60
gcttc                                                               65

<210> SEQ ID NO 13
<211> LENGTH: 65
<212> TYPE: DNA
<213> ORGANISM: Artificial Sequence
<220> FEATURE:
<223> OTHER INFORMATION: Primer pta-ackA-A

<400> SEQUENCE: 13
tcaggcagtc aggcggctcg cgtcttgcgc gataaccagt tcttccatat gaatatcctc    60
cttag                                                               65

<210> SEQ ID NO 14
<211> LENGTH: 31
<212> TYPE: DNA
<213> ORGANISM: Artificial Sequence
<220> FEATURE:
<223> OTHER INFORMATION: Primer pck-S

<400> SEQUENCE: 14
gggatccatg actgacttaa acaaaactcg t                                  31
```

<210> SEQ ID NO 15
<211> LENGTH: 32
<212> TYPE: DNA
<213> ORGANISM: Artificial Sequence
<220> FEATURE:
<223> OTHER INFORMATION: Primer pck-A

<400> SEQUENCE: 15
ccgctcgaga atacgaaaac ctggccgcgg tt                32

<210> SEQ ID NO 16
<211> LENGTH: 31
<212> TYPE: DNA
<213> ORGANISM: Artificial Sequence
<220> FEATURE:
<223> OTHER INFORMATION: Primer ptxD-S

<400> SEQUENCE: 16
actcgagatg ctgccgaaac tggtgatcac g                 31

<210> SEQ ID NO 17
<211> LENGTH: 30
<212> TYPE: DNA
<213> ORGANISM: Artificial Sequence
<220> FEATURE:
<223> OTHER INFORMATION: Primer ptxD-A

<400> SEQUENCE: 17
aagcttaatc gtgcggcgac caagccgaaa                   30

RECOMBINANT ESCHERICHIA COLI STRAIN FOR PRODUCING SUCCINIC ACID AND CONSTRUCTION METHOD THEREOF

This application is the National Stage Application of PCT/CN2020/128254, filed on Nov. 12, 2020, which claims priority to Chinese Patent Application No. 202011185169.0, filed on Oct. 29, 2020, which is incorporated by reference for all purposes as if fully set forth herein.

FIELD OF THE INVENTION

The present invention relates to the technical field of biological engineering, and more particularly to a recombinant *Escherichia coli* strain for efficiently producing succinic acid and a construction method thereof

DESCRIPTION OF THE RELATED ART

Succinic acid is an important C4 platform compound. As a starting material for the synthesis of general chemicals, succinic acid has a wide range of applications in food, chemistry, medicine and other fields. Succinic acid is listed by the US Department of Energy at the top place among the 12 most promising bulk bio-based chemicals.

Succinic acid is traditionally produced by chemical synthesis, mainly including paraffin oxidation, cyanidation and hydrolysis of methyl chloroacetate, and catalytic hydrogenation of vanadium pentoxide. However, due to the depletion of petroleum resources and the increasingly serious environmental pollution problems, the disadvantages of chemical synthesis become more and more notorious. The production of succinic acid by fermentation can get rid of the dependence on non-renewable strategic resource petroleum, and using renewable resources to fix carbon dioxide and reduce the greenhouse effect shows a prosperous development prospect. At present, the mostly extensively studied succinic acid-producing bacteria include *Actinobacillus succinogenes, Anaerobiospirillum succiniciproducens*, and *E. coli*. *Actinobacillus succinogenes* is usually screened from nature and directed engineered to tolerate high concentration of succinate. Mutant *Actinobacillus succinogenes* strain FZ53 is used by Guettler M et al. to produce succinic acid with a high yield, where glucose is used as a carbon source, and a maximum production reaches 110 g/L after fermentation for 48 h. There are few studies on the *Actinobacillus succinogenes* strains, and further research on their physiological characteristics, fermentation performance and genetic background is needed. *Anaerobiospirillum succiniciproducens* can make use of a wide range of fermentation substrates, such as glucose, lactose, and glycerol, etc. The research results of Samuelov et al. show that the production of succinic acid by *Anaerobiospirillum succiniciproducens* under optimal conditions can be up to 1.2 mol/1.0 mol glucose, and the highest production is 65.0 g/L. However, the fermentation with this strain requires a strict anaerobic environment, which is difficult to attain in industrial applications. As a type strain, *E. coli* has a clear genetic background and is easy to operate. The strain can be engineered by various molecular biology techniques. Therefore, the use of *E. coli* to produce succinic acid by fermentation has become a hot spot and many progresses have been made in the research. Recombinant *E. coli* strain AFP111 is used by Vemuri et al. in a two-stage method, and after fermentation for 76 h, the final concentration of succinic acid can reach 99.2 g/L, the yield is up to 1.1 g/g glucose, and the space time yield reaches 1.3 g/L/h. A recombinant *E. coli* strain HX024 is constructed by Zhang Xueli et al. by genetic engineering and adaptive evolution strategy, with which one-step anaerobic fermentation is performed for 96 h, to obtain a final succinic acid production up to 95.9 g/L and a yield of 1 g/g glucose. The ppc and pck genes are combinatorially optimized and expressed by Zhu Liwen et al. to enhance the $CO_2$ fixation pathway, and after fermentation with the recombinant *E. coli* strain AFP111 for 96 h, the succinic acid production reaches 90.7 g/L. The glucose absorption and metabolism pathway is optimized and the encoding gene of the by-product acetic acid is knocked out by Zhang Jianguo et al., and after fermentation for 65 h, the final succinic acid production reaches 98.92 g/L.

At present, the production efficiency by fermentation with *E. coli* is low. The fermentation broth usually contains by-products such as lactic acid, formic acid, acetic acid, ethanol, and others. The cofactor metabolism during the fermentation process is unbalanced, and the strain cannot tolerate high concentrations of the product and the substrate glucose, high osmotic pressure, and metabolic imbalance caused by rapid glucose absorption and utilization. The product yield and space time yield are low. To obtain a high-performance production strain, a combination method of traditional breeding, various omics analysis, and molecular biological engineering is generally used.

SUMMARY OF THE INVENTION

To solve the above problems, the present invention provides a recombinant *E. coli* strain for efficiently producing succinic acid. The pyruvate formate lyase coding gene pflB-focA, the lactate dehydrogenase coding gene ldhA, and the phosphotransacetylase coding gene pta in *E. coli* are knocked out from the host strain FMME-N-5 by the Red homologous recombination technology, and the key enzymes phosphoenolpyruvate carboxykinase pck and phosphite dehydrogenase ptxD involved in the succinate synthesis pathway are overexpressed.

A first object of the present invention is to provide a recombinant *E. coli* strain for efficiently producing succinic acid. The recombinant *E. coli* stain is obtained by knocking out one or more of the pyruvate formate lyase coding gene pflB-focA, the lactate dehydrogenase coding gene ldhA, and the phosphotransacetylase coding gene pta and overexpressing the phosphoenolpyruvate carboxykinase Pck and the phosphite dehydrogenase PtxD in *E. coli*.

Preferably, the nucleotide sequence of the gene encoding the phosphoenolpyruvate carboxykinase is as shown in SEQ ID NO:1, and the nucleotide sequence of the gene encoding the phosphite dehydrogenase is as shown in SEQ ID NO:2.

Preferably, the phosphoenolpyruvate carboxykinase pck and the phosphite dehydrogenase ptxD are expressed by the plasmid pTrcHisA.

Preferably, the nucleotide sequence of the pyruvate formate lyase coding gene pflB-focA is as shown in SEQ ID NO:3; the nucleotide sequence of the lactate dehydrogenase coding gene ldhA is as shown in SEQ ID NO:4; and the nucleotide sequence of the phosphotransacetylase coding gene pta is as shown in SEQ ID NO:5.

Preferably, the host of the recombinant *E. coli* strain is FMME-N-5, which was deposited in the China Center for Type Culture Collection (Address: Wuhan University, Wuhan, China) on Aug. 27, 2020, under CCTCC Accession NO: M 2020454.

The second object of the present invention is to provide a method for constructing a recombinant *E. coli* strain, which comprises the following steps:

(1) constructing pflB-focA, ldhA, and pta gene knockout frame fragments; sequentially transferring the gene knockout frame fragments into a host cell carrying the pKD46 plasmid, and screening to obtain a strain in which the target genes are knocked out; and (2) obtaining the gene fragments of the phosphoenolpyruvate carboxykinase pck and the phosphite dehydrogenase ptxD, ligating the gene fragments to an expression vector, and then transferring the expression vector ligated with the gene fragments to the strain in Step (1), to obtain the recombinant E. coli strain.

A third object of the present invention is to provide use of the E. coli strain in the production of succinic acid. The aerobic-anaerobic two-stage fermentation is carried out with the recombinant E. coli strain in a fermentation medium, to obtain a fermentation broth containing succinic acid.

Preferably, the fermentation medium includes: glucose 30-50 g/L, corn steep liquor 15-25 g/L, $(NH_4)_2SO_4$ 2-4 g/L, $K_2HPO_4$ 1.2-2.0 g/L, $KH_2PO_4$ 0.5-1.0 g/L, $MgSO_4.7H_2O$ 0.2-0.5 g/L, and NaCl 1-2 g/L.

Preferably, in the aerobic-anaerobic two-stage fermentation, the aerobic stage is shifted to the anaerobic stage when the bacterial cell suspension has an $OD_{600}$ of 52-60.

More preferably, the aerobic stage is shifted to the anaerobic stage by introducing $CO_2$ or adding 10-20 g/L bicarbonate.

Preferably, in the anaerobic stage, the glucose concentration is controlled to 5-15 g/L.

Preferably, the inoculation amount in the aerobic-anaerobic two-stage fermentation is 6-12 vol %; and the fermentation temperature is 35-38° C.

Preferably, the fermentation time of the aerobic-anaerobic two-stage fermentation is 50-96 h.

Preferably, in the anaerobic stage, a pH neutralizer is added, and the pH neutralizer is selected from the group consisting of $Na_2CO_3$, $K_2CO_3$, NaOH, KOH, $CaCO_3$, and basic magnesium carbonate and any combination thereof.

Preferably, after aerobic-anaerobic two-stage fermentation for 48 h, an osmotic protective agent is added, the osmotic protective agent is selected from the group consisting of proline, methionine, cysteine, betaine and any combination thereof.

In the present invention, the phosphite dehydrogenase (ptxD) can catalyze the conversion of phosphite into one molecule of phosphate, while consuming one molecule of $NAD^+$ to produce one molecule of NADH. The phosphate produced in this reaction has no inhibition on the cell growth and ptxD activity, and the reaction catalyzed by ptxD will not directly compete with the metabolites in the cell. Therefore, the expression of ptxD will increase the supply of NADH without affecting the main metabolic pathway for succinate production.

The present invention has the following beneficial effects.

In the present invention, the Red homologous recombination strategy is used to knock out the genes encoding related enzymes that affect succinic acid production, including the pyruvate formate lyase, the lactate dehydrogenase, and the phosphotransacetylase, so as to reduce the accumulation of by-products and facilitate the accumulation of succinic acid while the growth of the bacterial cells is not affected. Moreover, the phosphoenolpyruvate carboxykinase and the phosphite dehydrogenase involved in the succinate synthesis pathway are overexpressed, to effectively increase the production of succinic acid. Finally, an engineered strain E. coli FMME-N-5(ΔfocA-pflB-ΔldhA-Δpta)-pck-ptxD is obtained. After fermentation with the strain for 96 h, the production of succinic acid reaches 137 g/L, the yield of succinic acid is up to 1 g/g glucose, and the space time yield is 1.43 g/L/h, while no by-products lactic acid and formic acid are accumulated, and the acetic acid content is less than 10 g/L. The strain constructed in the present invention is beneficial to the industrial production of succinic acid.

Deposit of Biological Material

The E. coli strain FMME-N-5 was deposited in the China Center for Type Culture Collection (Address: Wuhan University, Wuhan, China) on Aug. 27, 2020, under CCTCC Accession NO: M 2020454.

DETAILED DESCRIPTION OF THE PREFERRED EMBODIMENTS

The present invention will be further described below in connection with specific examples, so that those skilled in the art can better understand and implement the present invention; however, the present invention is not limited thereto.

Unmentioned nucleotide sequence information in the Sequence Listing:

(1) SEQ ID NO:1 is the nucleotide sequence of *Actinobacillus succinogenes*-derived phosphoenolpyruvate carboxykinase pck coding gene;

(2) SEQ ID NO:2 is the nucleotide sequence of *Pseudomonas stutzeri*-derived phosphite dehydrogenase ptxD coding gene;

(3) SEQ ID NO:3 is the nucleotide sequence of pyruvate formate lyase coding gene pflB-focA;

(4) SEQ ID NO:4 is the nucleotide sequence of lactate dehydrogenase coding gene ldhA; and (5) SEQ ID NO:5 is the nucleotide sequence of phosphotransacetylase coding gene pta.

Determination of Bacterial Cell Density:

An appropriate amount of fermentation broth is neutralized with 2 mol/L hydrochloric acid, and the cell density is expressed by the absorbance measured by a spectrophotometer at a wavelength of 600 nm.

Determination of Glucose:

Pretreatment of fermentation broth: The fermentation broth is centrifuged at 12000 r/min for 5 min, and the supernatant is collected. After dilution by an appropriate factor, the glucose concentration in the fermentation broth is determined by M-100 biosensor analyzer.

Determination of Organic Acids:

High performance liquid chromatography: Pretreatment of fermentation broth: The fermentation broth is centrifuged at 12000 r/min for 5 min, and the supernatant is collected. After dilution by an appropriate factor, the production of succinic acid, lactic acid, formic acid, and acetic acid is detected by high performance liquid chromatography (HPLC). The instrument is Waters e2695 reversed-phase high performance liquid chromatograph, the chromatographic column is Bio-Rad HPX 87H; the mobile phase is 5 mmoL/L H$_2$SO$_4$, the flow rate is set to 0.6 mL/min; the detector is a UV detector; the detection wavelength is 210 nm, and the column temperature is 35° C.

Example 1: Knockout of Pyruvate Formate Lyase Coding Gene (1) To knock out the gene encoding pyruvate formate lyase to reduce the amount of the by-product formic acid, a gene editing fragment was constructed by the Red homologous recombination technology. The gene editing fragment includes upstream and downstream homologous arm regions, and a resistance screening cassette. Using the plasmid pKD4 as a template, the resistance screening gene Kan was amplified with designed primer pair pflB-focA-S/pflB-focA-A as shown in SEQ ID NO:6/SEQ ID NO:7, to obtain a pflB-focA knockout frame fragment.

(2) The pKD46 plasmid was transformed into the expression host *E. coli* FMME-N-5 competent cells, and a recombinant strain *E. coli* FMME-N-5-pKD46 was screened out by colony PCR. The obtained pflB-focA knockout frame fragment was transferred into competent cells of the recombinant strain *E. coli* FMME-N-5-pKD46 by electroporation, and a positive transformant was obtained by screening in a plate containing 50 μg/mL Kan. Finally, the temperature-sensitive plasmid pCP20 was used to thermally induce the expression of FLP recombinase to remove the Kan resistance gene, and the cells were subcultured three times at 42° C., to remove the temperature-sensitive plasmids pKD46 and pCP20. In this way, *E. coli* FMME-N-5 (ΔfocA-pflB) in which pyruvate formate lyase coding gene was knocked out was successfully obtained.

```
Primer sequence information: 5'→3' direction
pflB-focA-S:
TTACTCCGTATTTGCATAAAAACCATGCGAGTTACGGGCC

TATAAGTGTAGGCTGGAGCTGCTTC pflB-focA-A:
ATAGATTGAGTGAAGGTACGAGTAATAACGTCCTGCTGCT

GTTCTCATATGAATATCCTCCTTAG
```

Example 2: Knockout of Lactate Dehydrogenase Expressing Gene (1) The construction of *E. coli* FMME-N-5 (ΔfocA-pflB) was the same as in Example 1.

To knock out the gene encoding lactate dehydrogenase to further reduce the amount of the by-product lactic acid, a gene editing fragment was constructed by the Red homologous recombination technology. The gene editing fragment includes upstream and downstream homologous arm regions, and a resistance screening cassette. Using the plasmid pKD4 as a template, the resistance screening gene Kan was amplified with designed primer pair ldhA-S/ldhA-A as shown in SEQ ID NO:8/SEQ ID NO:9, to obtain a ldhA knockout frame fragment.

(3) The pKD46 plasmid was transformed into the expression host *E. coli* FMME-N-5-ΔfocA-pflB competent cells, and a recombinant strain *E. coli* FMME-N-5-ΔfocA-pflB-pKD46 was screened out by colony PCR. The obtained ldhA knockout frame fragment was transferred into competent cells of the recombinant strain *E. coli* FMME-N-5-ΔfocA-pflB-pKD46 by electroporation, and a positive transformant was obtained by screening in a plate containing 50 μg/mL Kan. Finally, the temperature-sensitive plasmid pCP20 was used to thermally induce the expression of FLP recombinase to remove the Kan resistance gene, and the cells were subcultured three times at 42° C., to remove the temperature-sensitive plasmids pKD46 and pCP20. In this way, *E. coli* FMME-N-5 (ΔfocA-pflB-ΔldhA) in which lactate dehydrogenase coding gene was knocked out was successfully obtained.

```
Primer sequence information: 5'→3' direction
ldhA-S:
ATGAACTCGCCGTTTTATAGCACAAAACAGTACGACAAGAA

GTACGTGTAGGCTGGAGCTGCTTC ldhA-A:
TTAAACCAGTTCGTTCGGGCAGGTTTCGCCTTTTTCCAGAT

TGCTCATATGAATATCCTCCTTAG
```

Example 3: Knockout of Phosphotransacetylase Expressing Gene (1) The construction of *E. coli* FMME-N-5 (ΔfocA-pflB-ΔldhA) was the same as in Example 2.

(2) To knock out the gene encoding phosphotransacetylase to further reduce the amount of the by-product acetic acid while the growth of cells is ensured, a gene editing fragment was constructed by the Red homologous recombination technology. The gene editing fragment includes upstream and downstream homologous arm regions, and a resistance screening cassette. Using the plasmid pKD4 as a template, the resistance screening gene Kan was amplified with designed primer pair pta-S/pta-A as shown in SEQ ID NO:10/SEQ ID NO:11, to obtain a pta knockout frame fragment.

The pKD46 plasmid was transformed into the expression host *E. coli* FMME-N-5-ΔfocA-pflB-ΔldhA competent cells, and a recombinant strain *E. coli* FMME-N-5-ΔfocA-pflB-ΔldhA-pKD46 was screened out by colony PCR. The obtained pta knockout frame fragment was transferred into competent cells of the recombinant strain *E. coli* FMME-N-5-ΔfocA-pflB-ΔldhA-pKD46 by electroporation, and a positive transformant was obtained by screening in a plate containing 50 μg/mL Kan. Finally, the temperature-sensitive plasmid pCP20 was used to thermally induce the expression of FLP recombinase to remove the Kan resistance gene, and the cells were subcultured three times at 42° C., to remove the temperature-sensitive plasmids pKD46 and pCP20. In this way, *E. coli* FMME-N-5 (ΔfocA-pflB-ΔldhA-Δpta) in which phosphotransacetylase coding gene was knocked out was successfully obtained.

```
Primer sequence information: 5'→3' direction
pta-S:
GTGTCCCGTATTATTATGCTGATCCCTACCGGAACCAGCGT

CGGTCGTGTAGGCTGGAGCTGCTTC pta-A:
TACACCATCGCGCTGACTGCGATTCAGTCTGCACAGCAGCA

GCAGTAACATATGAATATCCTCCTTAG
```

Example 4: Knockout of Phosphotransacetylase-Acetokinase Expressing Gene (1) The construction of E. coli FMME-N-5 (ΔfocA-pflB-ΔldhA-Δpta) was the same as in Example 3.

To further reduce the amount of the by-product lactic acid, a gene editing fragment was constructed by the Red homologous recombination technology. The gene editing fragment includes upstream and downstream homologous arm regions, and a resistance screening cassette. Using the plasmid pKD4 as a template, the resistance screening gene Kan was amplified with designed primer pair pta-ackA-S/pta-ackA-A as shown in SEQ ID NO:12/SEQ ID NO:13, to obtain a pta-ackA knockout frame fragment.

The pKD46 plasmid was transformed into the expression host E. coli FMME-N-5-ΔfocA-pflB-ΔldhA-Δpta competent cells, and a recombinant strain E. coli FMME-N-5-ΔfocA-pflB-ΔldhA-pKD46 was screened out by colony PCR. The obtained pta-ackA knockout frame fragment was transferred into competent cells of the recombinant strain E. coli FMME-N-5-ΔfocA-pflB-ΔldhA-pKD46 by electroporation, and a positive transformant was obtained by screening in a plate containing 50 μg/mL Kan. Finally, the temperature-sensitive plasmid pCP20 was used to thermally induce the expression of FLP recombinase to remove the Kan resistance gene, and the cells were subcultured three times at 42° C., to remove the temperature-sensitive plasmids pKD46 and pCP20. In this way, E. coli FMME-N-5 (ΔfocA-pflB-ΔldhA-Δpta-ackA) in which phosphotransacetylase-acetokinase expressing gene was knocked out was successfully obtained.

```
Primer sequence information: 5'→3' direction
pta-ackA-S:
ATGTCGAGTAAGTTAGTACTGGTTCTGAACTGCGGTAGTTC

TTCAGTGTAGGCTGGAGCTGCTTC pta-ackA-A:
TCAGGCAGTCAGGCGGCTCGCGTCTTGCGCGATAACCAGTT

CTTCCATATGAATATCCTCCTTAG
```

Example 5: Construction of Expression Vector pTrcHisA-Pck

The phosphoenolpyruvate carboxykinase pck used in the present invention was derived from *Actinobacillus succinogenes*. The genomic DNA of *Actinobacillus succinogenes* was extracted.

According to the published genome sequence information, primer pair pck-S/pck-A with a sequence as shown in SEQ ID NO:14/SEQ ID NO:15 was designed. Using the genomic DNA extracted from *Actinobacillus succinogenes* as a template, the pck gene was obtained by amplification using a standard PCR amplification system and procedure.

```
pck-S :
GGGATCCATGACTGACTTAAACAAACTCGTT pck-A:
CCGCTCGAGAATACGAAAACCTGGCCGCGGTT
```

The pck obtained by PCR amplification was extracted and recovered by agarose gel nucleic acid electrophoresis. The recovered product and the expression vector pTrcHisA were digested with restriction endonuclease BamH I and XhoI for 3 hrs, and the digested product was recovered by agarose gel nucleic acid electrophoresis. The DNA and linearized plasmid were 1617 and 4405 bp, respectively, which were then ligated overnight at 16° C. with T4 DNA ligase and transformed into JM109 competent cells. Single colonies were picked up for verification by PCR, and the positive transformant was sequenced to be correct, which indicates that the expression vector was constructed successfully. The plasmid was designated as pTrcHisA-pck.

Example 6: Construction of Expression Vector pTrcHisA-Pck-ptxD

The phosphite dehydrogenase ptxD used in the present invention was derived from *Pseudomonas stutzeri*. The genomic DNA of *Pseudomonas stutzeri* was extracted.

According to the published genome sequence information, primer pair ptxD-S/ptxD-A with a sequence as shown in SEQ ID NO:16/SEQ ID NO:17 was designed. Using the genomic DNA extracted from *Pseudomonas stutzeri* as a template, the ptxD gene was obtained by amplification using a standard PCR amplification system and procedure.

```
Primer sequence information: 5'→3' direction:
ptxD-S:
ACTCGAGATGCTGCCGAAACTGGTGATCACG ptxD-A:
AAGCTTAATCGTGCGGCGACCAAGCCGAAA
```

The ptxD obtained by PCR amplification was extracted and recovered by agarose gel nucleic acid electrophoresis. The recovered product and the expression vector pTrcHisA-pck were digested with restriction endonuclease XhoI and Hind III for 3 h, and the digested product was recovered by agarose gel nucleic acid electrophoresis. The DNA and linearized plasmid were 1011 and 4370 bp, respectively, which were then ligated overnight at 16° C. with T4 DNA ligase and transformed into JM109 competent cells. Single colonies were picked up for verification by PCR, and the positive transformant was sequenced to be correct, which indicates that the expression vector was constructed successfully. The plasmid was designated as pTrcHisA-pck-ptxD. The recombinant plasmid was electroporated into the expression host E. coli FMME-N-5 (ΔfocA-pflB-ΔldhA-Δpta-ackA), to obtain the recombinant strain E. coli FMME-N-5 (ΔfocA-pflB-ΔldhA-Δpta-ackA)-pck-ptxD.

Example 7: Fed-Batch Fermentation with Recombinant E. coli Strain FMME-N-5 (ΔfocA-pflB-ΔldhA-ΔPta-ackA)-Pck-ptxD in a Fermentor The fermentation medium in the fermentor includes glucose 35 g/L, corn steep liquor 20 g/L, $(NH_4)_2SO_4$ 3 g/L, $K_2HPO_4$ 1.4 g/L, $KH_2PO_4$ 0.6 g/L, $MgSO_4 \cdot 7H_2O$ 0.5 g/L, and NaCl 2 g/L; and the fed-batch medium comprises glucose 800 g/L.

The recombinant E. coli strain FMME-N-5-ΔfocA-pflB-ΔldhA-Δpta-pck-ptxD was picked up for two-stage fermentation in a 7.5 L fermentor. The single colonies were inoculated in 25 mL LB medium (in 50 mL shake flask) and used as the primary seed culture, and then cultured at 38° C. and 200 rpm for 8.5 h. 200 μl of the primary seed culture was inoculated into a seed medium in an amount of 50 mL/500 mL, and cultured at 38° C. and 200 rpm for 7.5 h to obtain a secondary seed culture. The initial liquid volume in the fermentor was 4 L, and the inoculation amount of the seed culture was 10%. The fermentation conditions in the aerobic stage were as follows. The culture temperature was 38° C., the air flow rate for aeration was 1 vvm, the initial stirring speed was 600 r/min, the pH was controlled to 7.0 with ammonia, and the dissolved oxygen in the whole aerobic stage was controlled at a level of 20%. The process was shifted to the anaerobic fermentation stage when the bacterial cell density was grown to an $OD_{600}$ of 55-60. In the anaerobic stage, aeration was stopped, the stirring speed was 200 r/min, 800 g/L glucose was fed and the feed rate was controlled to control the pH of the fermentation broth to be less than 10 g/L. Basic magnesium carbonate was used to control the pH to 6.5 in the anaerobic stage. The fermentation period was 96 h in total.

Figure 1:
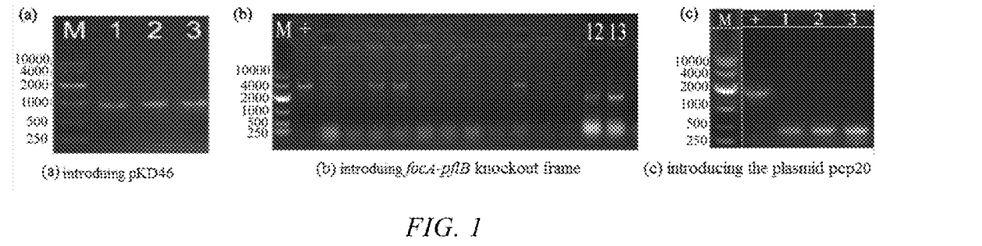
FIG. 1 is a gel electrophoretogram for verifying the knock-out of pyruvate formate lyase coding gene.
Figure 2:
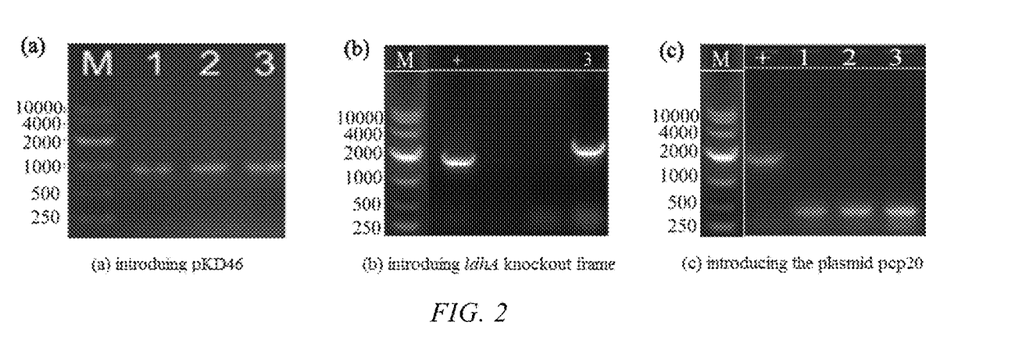
FIG. 2 is a gel electrophoretogram for verifying the knock-out of lactate dehydrogenase coding gene.
Figure 3:
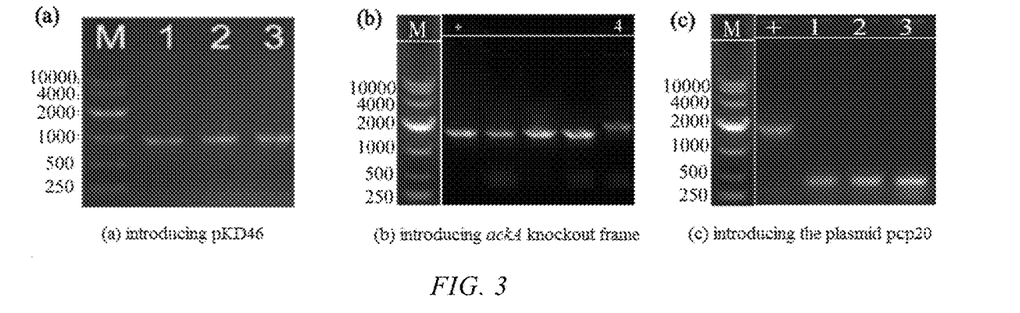
FIG. 3 is a gel electrophoretogram for verifying the knock-out of phosphotransacetylase coding gene.
Figure 4:
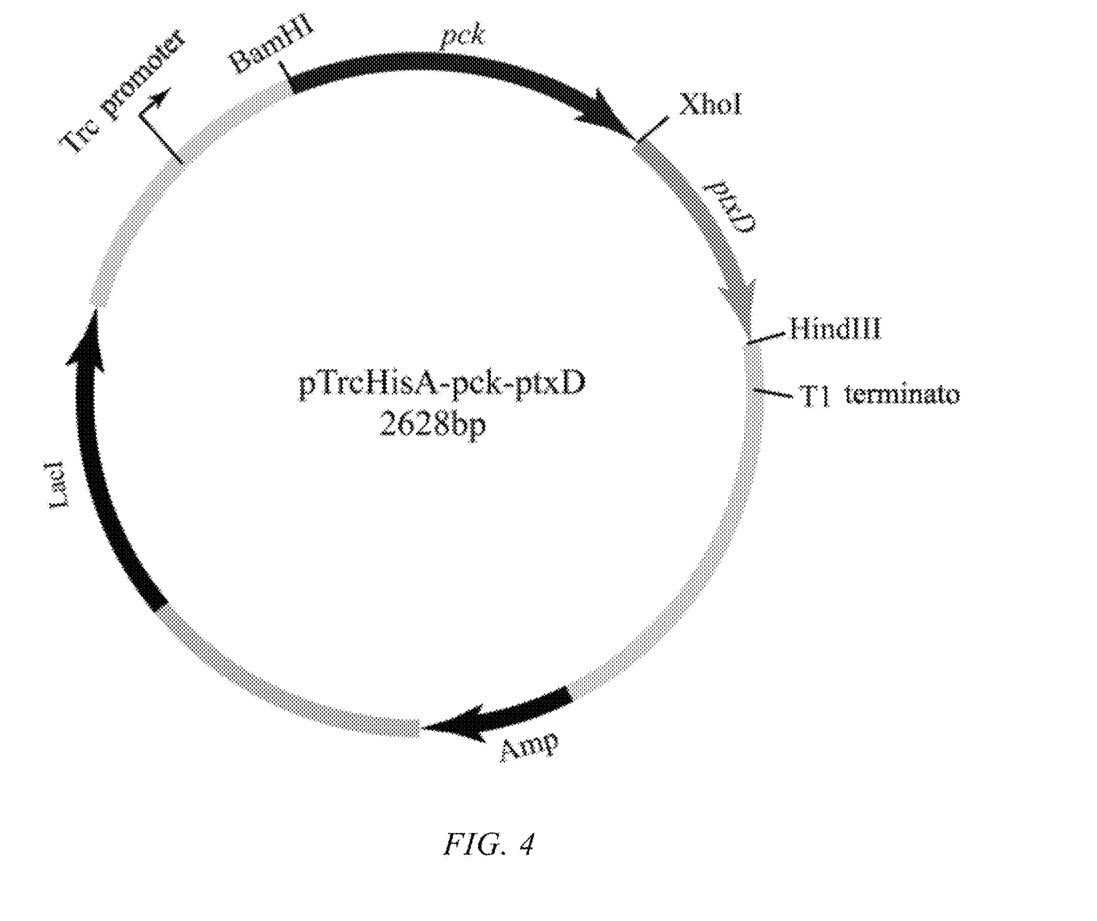
FIG. 4 is a map of a recombinant vector expressing phosphoenolpyruvate carboxykinase and phosphite dehydrogenase.
Figure 5:
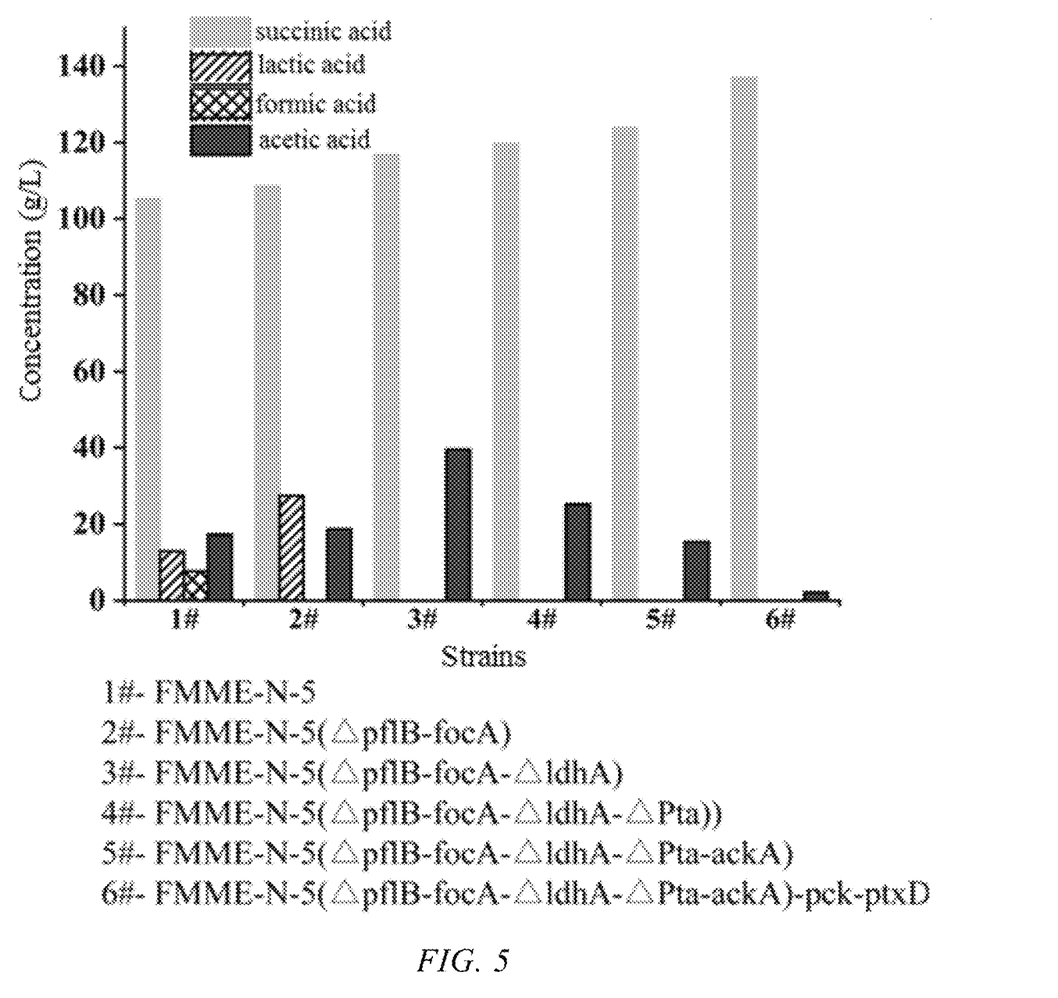
FIG. 5 shows the results of 96-h fed-batch fermentation with the constructed engineered strain E. coli FMME-N-5 (ΔfocA-pflB-ΔldhA-Δpta)-pck-ptxD in a fermentor.

The test result of the production of succinic acid is shown in FIG. 5. After 96 h of fermentation, the production of succinic acid by the recombinant *E. coli* strain FMME-N-5-ΔfocA-pflB-ΔldhA-Δpta-pck-ptxD is up to 137 g/L, the yield of succinic acid is 1 g/g glucose, and the space time yield is 1.43 g/L/h, while no by-products lactic acid and formic acid are accumulated, and the acetic acid content is only 1-2 g/L.

The above results indicate that in the present invention, related by-product coding genes including pyruvate formate lyase coding gene focA-pflB, lactate dehydrogenase coding gene ldhA, and phosphotransacetylase coding gene pta are knocked out, and the phosphoenolpyruvate carboxykinase pck and the phosphite dehydrogenase ptxD involved in the succinate synthesis pathway are overexpressed by genetic engineering technologies to balance the cofactor metabolism, thereby effectively improving the production of succinic acid.

The above-described embodiments are merely preferred embodiments for the purpose of fully illustrating the present invention, and the scope of the present invention is not limited thereto. Equivalent substitutions or modifications can be made by those skilled in the art based on the present invention, which are within the scope of the present invention as defined by the claims.

What is claimed is:

1. A recombinant *Escherichia coli* strain for producing succinic acid, wherein the recombinant *Escherichia coli* stain is obtained by knocking out one or more of the pyruvate formate lyase coding gene pflB-focA, the lactate dehydrogenase coding gene ldhA, and the phosphotransacetylase coding gene pta, and overexpressing the phosphoenolpyruvate carboxykinase gene Pck and the phosphite dehydrogenase gene PtxD in *Escherichia coli*.

2. The recombinant *Escherichia coli* strain according to claim 1, wherein a nucleotide sequence of the gene encoding the phosphoenolpyruvate carboxykinase is as shown in SEQ ID NO:1, and a nucleotide sequence of the gene encoding the phosphite dehydrogenase is as shown in SEQ ID NO:2.

3. The recombinant *Escherichia coli* strain according to claim 1, wherein the phosphoenolpyruvate carboxykinase pck and the phosphite dehydrogenase ptxD are expressed by a plasmid pTrcHisA.

4. The recombinant *Escherichia coli* strain according to claim 1, wherein a host of the recombinant *Escherichia coli* strain is *Escherichia coli* FMME-N-5, which was deposited in the China Center for Type Culture Collection (Address: Wuhan University, Wuhan, China) on Aug. 27, 2020, under CCTCC Accession NO: M 2020454.

5. A method for constructing a recombinant *Escherichia coli* strain according to claim 1, comprising steps of:
   (1) constructing pflB-focA, ldhA, and pta gene knockout frame fragments; sequentially transferring the gene knockout frame fragments into a host cell carrying the pKD46 plasmid, and screening to obtain a strain wherein the target genes are knocked out; and
   (2) obtaining the gene fragments of the phosphoenolpyruvate carboxykinase pck and the phosphite dehydrogenase ptxD, ligating the gene fragments to an expression vector, and then transferring the expression vector ligated with the gene fragments to the strain in Step (1), to obtain the recombinant *Escherichia coli* strain.

6. A method of production of succinic acid comprising the use of the *Escherichia coli* strain according to claim 1 in the production of succinic acid, wherein aerobic-anaerobic two-stage fermentation is carried out with the recombinant *Escherichia coli* strain in a fermentation medium, to obtain a fermentation broth containing succinic acid.

7. The method according to claim 6, wherein in the aerobic-anaerobic two-stage fermentation, the aerobic stage is shifted to the anaerobic stage when the bacterial cell suspension has an $OD_{600}$ of 52-60.

8. The method according to claim 6, wherein the aerobic stage is shifted to the anaerobic stage by introducing $CO_2$ or adding 10-20 g/L bicarbonate.

9. The method according to claim 6, wherein in the anaerobic stage, the glucose concentration is controlled to 5-15 g/L.

10. The method according to claim 6, wherein the inoculation amount in the aerobic-anaerobic two-stage fermentation is 6-12 vol %; and the fermentation temperature is 35-38° C.

* * * * *